United States Patent
Mitchell et al.

(10) Patent No.: US 12,168,647 B2
(45) Date of Patent: Dec. 17, 2024

(54) FUNCTIONALIZED TRIAZINE COMPOUNDS, COMPOSITIONS COMPRISING SUCH COMPOUNDS AND CURED FLUOROPOLYMER ARTICLES

(71) Applicant: 3M INNOVATIVE PROPERTIES COMPANY, St. Paul, MN (US)

(72) Inventors: Michael H. Mitchell, Edina, MN (US); Tatsuo Fukushi, Woodbury, MN (US); Miguel A. Guerra, Woodbury, MN (US); Zai-Ming Qiu, Woodbury, MN (US); Justin T. Roop, Madison, AL (US)

(73) Assignee: 3M Innovative Properties Company, St. Paul, MN (US)

( * ) Notice: Subject to any disclaimer, the term of this patent is extended or adjusted under 35 U.S.C. 154(b) by 548 days.

(21) Appl. No.: 17/615,155

(22) PCT Filed: Jun. 22, 2020

(86) PCT No.: PCT/IB2020/055861
§ 371 (c)(1),
(2) Date: Nov. 30, 2021

(87) PCT Pub. No.: WO2020/261089
PCT Pub. Date: Dec. 30, 2020

(65) Prior Publication Data
US 2022/0235016 A1    Jul. 28, 2022

Related U.S. Application Data

(60) Provisional application No. 62/868,041, filed on Jun. 28, 2019.

(51) Int. Cl.
C08K 5/3492 (2006.01)
C07D 251/24 (2006.01)
C08K 5/14 (2006.01)

(52) U.S. Cl.
CPC .......... *C07D 251/24* (2013.01); *C08K 5/3492* (2013.01); *C08K 5/14* (2013.01)

(58) Field of Classification Search
CPC ...... C07D 251/14; C08K 5/3492; C08K 5/14; C08L 29/10; C08L 27/20
USPC ...................................................... 524/100
See application file for complete search history.

(56) References Cited

U.S. PATENT DOCUMENTS

| | | | |
|---|---|---|---|
| 5,225,504 A | 7/1993 | Tatsu | |
| 6,191,233 B1 | 2/2001 | Kishine | |
| 6,887,927 B2 | 5/2005 | Grootaert et al. | |
| 7,592,386 B2 | 9/2009 | Grootaert et al. | |
| 2003/0096930 A1 | 5/2003 | Wlassics | |
| 2004/0116742 A1 | 6/2004 | Guerra | |
| 2008/0021148 A1 | 1/2008 | Adair | |
| 2014/0011933 A1* | 1/2014 | Shefelbine | C08F 214/184 524/413 |
| 2018/0194888 A1 | 7/2018 | Mitchell | |

FOREIGN PATENT DOCUMENTS

| | | |
|---|---|---|
| CN | 1678672 A | 10/2005 |
| CN | 101541882 A | 9/2009 |
| JP | S 55-17336 A | 2/1980 |
| JP | H06340710 | 12/1994 |
| WO | WO1997-005122 | 2/1997 |
| WO | WO2012-072532 | 6/2012 |
| WO | WO2014-200973 | 12/2014 |
| WO | WO2018-136324 | 7/2018 |
| WO | WO2018-136331 | 7/2018 |
| WO | WO2018-136332 | 7/2018 |
| WO | WO2019-155073 | 8/2019 |

OTHER PUBLICATIONS

Tumanova, "Reaction of trifluoromethyl triflorovinyl ether with nucleophilic reagents", 1965, vol. 35, No. 2, pp. 399-400.
Tumanova, "Reaction of perfluoromethyl perfluorovinyl ether and nucleophiles", Database Chemabs [Online] Chemical Abstracts Service. Columbus. Ohio, US, XP002800087, Database accession No. 1965.74219, Apr. 22, 2001, 1 page.
International Search report for PCT International Application No. PCT/IB2020/055861 mailed on Sep. 8, 2020, 5 pages.

* cited by examiner

*Primary Examiner* — Ruiyun Zhang
(74) *Attorney, Agent, or Firm* — Julie Lapos-Kuchar

(57) ABSTRACT

Described herein are compounds according to Formula (I) wherein Rf is a perfluorinated divalent group comprising 2 to 12 carbon atoms; and Z is selected from —CH=CH$_2$, and —CH$_2$CH=CH. A method of making the compound from a functionalized vinyl ether and ammonia is disclosed. In one embodiment, the functionalized triazine-containing compound is used in the polymerization of a fluoropolymer. In another embodiment, the functionalized triazine-containing compound is used in a curable fluoropolymer composition and cured to form articles.

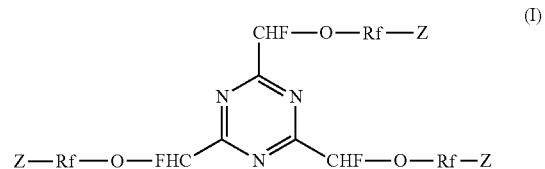

(I)

18 Claims, No Drawings

FUNCTIONALIZED TRIAZINE COMPOUNDS, COMPOSITIONS COMPRISING SUCH COMPOUNDS AND CURED FLUOROPOLYMER ARTICLES

TECHNICAL FIELD

A triazine compound functionalized with a halogen, vinyl, or allyl group is described along with a method of making such compounds. Also described are curable fluoropolymer compositions comprising such compounds and cured articles therefrom, as well as polymers derived from such compounds.

SUMMARY

There is a desire to identify novel compounds, which can be used in the curing of fluoropolymers. In some embodiments, the compounds have better compatibility with the fluoropolymers. In some embodiments, the resulting cured polymers have improved properties.

In one aspect, compound according to Formula (I) is described,

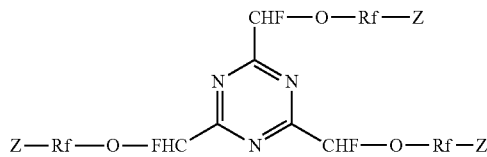

wherein Rf is selected from a perfluorinated divalent group comprising 2 to 12 carbon atoms; and Z is selected from —I, —Br, —CH=CH$_2$, and —CH$_2$CH=CH$_2$ In another embodiment, the compound according to Formula (I) can be used in a polymerization of a fluoropolymer.

In another embodiment, the compound according to Formula (I) can be used in the peroxide curing of a fluoropolymer.

In another aspect, a method of making a triazine-containing compound is described, the method comprising reacting ammonia with a functionalized perfluorovinyl ether of Formula (II)

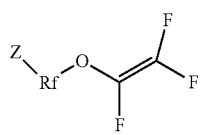

wherein Rf is selected from a perfluorinated divalent group comprising 2 to 12 carbon atoms; and Z is selected from —I, —Br, —CH=CH$_2$, —CH$_2$CH=CH$_2$, and —CH$_2$OH to form a nitrile derivative;
reacting ammonia with the nitrile derivative to form an amidine derivative; and
heating the amidine derivative to generate a compound according to Formula (I)

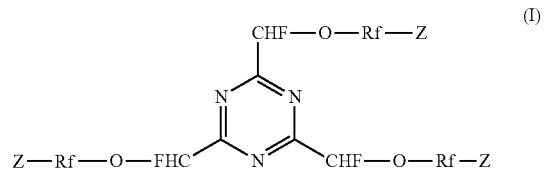

wherein Rf is a perfluorinated divalent group comprising 2 to 12 carbon atoms; and Z is selected from —I, —Br, —CH=CH$_2$, and —CH$_2$CH=CH$_2$.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more; and
"and/or" is used to indicate one or both stated cases may occur, for example A and/or B includes, (A and B) and (A or B);
"backbone" refers to the main continuous chain of the polymer;
"crosslinking" refers to connecting two pre-formed polymer chains using chemical bonds or chemical groups;
"cure site" refers to functional groups, which may participate in crosslinking;
"interpolymerized" refers to monomers that are polymerized together to form a polymer backbone;
"monomer" is a molecule which can undergo polymerization which then form part of the essential structure of a polymer;
"perfluorinated" means a group or a compound derived from a hydrocarbon wherein all hydrogen atoms have been replaced by fluorine atoms. A perfluorinated compound may however still contain other atoms than fluorine and carbon atoms, like oxygen atoms, chlorine atoms, bromine atoms and iodine atoms; and
"polymer" refers to a macrostructure having a number average molecular weight (Mn) of at least 30,000 dalton, at least 50,000 dalton, at least 100,000 dalton, at least 300,000 dalton, at least 500,000 dalton, at least, 750,000 dalton, at least 1,000,000 dalton, or even at least 1,500,000 dalton and not such a high molecular weight as to cause premature gelling of the polymer.

Also herein, recitation of ranges by endpoints includes all numbers subsumed within that range (e.g., 1 to 10 includes 1.4, 1.9, 2.33, 5.75, 9.98, etc.).

Also herein, recitation of "at least" followed by a number includes all numbers including the specific number and those greater (e.g., "at least 1" includes at least 2, at least 4, at least 6, at least 8, at least 10, at least 25, at least 50, at least 100, etc.).

As used herein, "comprises at least one of" A, B, and C refers to element A by itself, element B by itself, element C by itself, A and B, A and C, B and C, and a combination of all three.

The present disclosure is directed toward a compound according to Formula (I), along with a method of making such a compound, as well as their use in fluoropolymer compositions.

Functionalized Triazine-Containing Compound

The functionalized triazine compounds of the present disclosure are molecules according to Formula (I): [Z—Rf—O—CFH]$_3$—C$_3$N$_3$, or

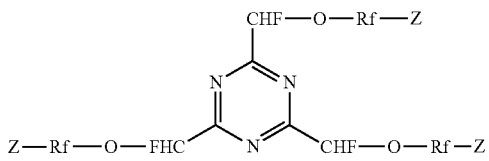

wherein Rf is a perfluorinated divalent group comprising 2 to 12 carbon atoms; and Z is selected from —I, —Br, —CH=CH$_2$, —CH$_2$CH=CH$_2$, CH$_2$OH, —SO$_2$NH$_2$ and derivatives thereof (such as —SO$_2$F), and —CONH$_2$ and derivatives thereof (such as —CO$_2$CH$_3$).

Rf is a divalent perfluorinated group comprising 2 to 12 carbon atoms. In one embodiment Rf comprises at least 2, 3, 4, 5, 6, or even 8 carbon atoms. In one embodiment Rf comprises at most 6, 8, 10 or even 12 carbon atoms. Rf may be linear, branched, and/or cyclic in nature. In one embodiment, Rf is a linear alkylene, such as —(CF$_2$)$_n$—, where n is an integer of at least 2, 3, or even 4; and at most 5, 6, 7, or even 8. In one embodiment, Rf is a branched alkylene such as —[(CF$_2$CF(CF$_3$)]$_n$)—, where n is an integer of at least 2, 3, 4; and at most 5, 6, 7, or even 8.

Rf may optionally contain at least one catenated oxygen (i.e., ether) and/or nitrogen (i.e., amine) atom. For example, Rf may comprise —(CF$_2$)$_p$—O—(CF$_2$)$_q$—, —(OCF$_2$CF$_2$)$_q$—, —(OCF$_2$CF(CF$_3$))$_p$— and/or —(CF$_2$CF(CF$_3$))$_p$—O—(CF$_2$)$_q$—, wherein p is an integer of 1, 2, 3, 4, 5, 6, 7, 8, 9, 10 or 11 and q is an integer from 1, 2, 3, 4, 5, 6, 7, 8, 9, 10 or 11, such that the sum of p+q is 2, 3, 4, 5, 6, 7, 8, 9, 10, 1, or 12.

It should be appreciated that irrespective of what is depicted in any of the chemical structures shown, no representations are made regarding the stereoisomerism of the compounds and their spatial arrangement of atoms.

The compounds according to Formula (I) are small molecules, having a molecular weight of at least 600 g/mole and less than 5000, 4000, 3000, 2500, 2200, 2000, 1800, 1500, 1200, or even 1000 grams/mole.

Exemplary compounds of Formula (I) include: [Br—(CF$_2$)$_4$OCFH]$_3$—C$_3$N$_3$, [I—(CF$_2$)$_4$OCFH]$_3$—C$_3$N$_3$, [CH$_2$=CH—(CF$_2$)$_4$OCFH]$_3$—C$_3$N$_3$, [CH$_2$=CHCH$_2$—(CF$_2$)$_4$OCFH]$_3$—C$_3$N$_3$, [CH$_2$=CH—(CF$_2$)$_2$OCF(CF$_3$)CF$_2$OCFH]$_3$—C$_3$N$_3$, [CH$_2$=CHCH$_2$—(CF$_2$)$_2$OCF(CF$_3$)CF$_2$OCFH]$_3$—C$_3$N$_3$, [Br—(CF$_2$)$_2$OCF(CF$_3$)CF$_2$OCFH]$_3$—C$_3$N$_3$, and [I—(CF$_2$)$_2$OCF(CF$_3$)CF$_2$OCFH]$_3$—C$_3$N$_3$, where C$_3$N$_3$ represents the triazine ring.

Method of Making

The compounds according to Formula (I) may be made by reacting a vinyl ether monomer with three equivalents of ammonia to 1 mole of Formula (II) to form a nitrile molecule of Formula (III). The amidine molecule of Formula (IV) can be derived by adding another mole of ammonia to the nitrile molecule of Formula (III) or adding excess ammonia to Formula (II) to isolate the amidine molecule directly. The amidine molecule of Formula (IV) can then be heated to arrive at the compound according to Formula (I). The proposed reaction scheme is shown below:

Z—Rf—O—CF=CF$_2$+3NH$_3$→Z—Rf—O—CHF—C≡N+2HF·NH$_3$

Z—Rf—O—CHF—CN+NH$_3$→Z—Rf—O—CHF—C(=NH)NH$_2$

3[Z—Rf—O—CHF—C(=NH)NH$_2$]+heat→Formula (I)+3NH$_3$ where Rf and Z are the same as defined above.

The vinyl ether monomers used as a starting material are according to Formula (II):

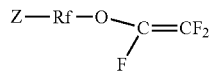

wherein Rf is a perfluorinated divalent group as described above, and Z is selected from —I, —Br, —CH=CH$_2$, —CH$_2$CH=CH$_2$, —SO$_2$NH$_2$ and —CONH$_2$.

Exemplary vinyl ether monomers according to Formula (II) include: Br(CF$_2$)$_4$OCF=CF$_2$, I(CF$_2$)$_4$OCF=CF$_2$, CH$_2$=CH(CF$_2$)$_4$OCF=CF$_2$, CH$_2$=CHCH$_2$(CF$_2$)$_4$OCF=CF$_2$, Br(CF$_2$)$_5$OCF=CF$_2$, I(CF$_2$)$_5$OCF=CF$_2$, CH$_2$=CH(CF$_2$)$_5$OCF=CF$_2$, CH$_2$=CHCH$_2$(CF$_2$)$_5$OCF=CF$_2$, CH$_2$=CH(CF$_2$)$_2$OCF(CF$_3$)CF$_2$OCF=CF$_2$, CH$_2$=CHCH$_2$(CF$_2$)$_2$OCF(CF$_3$)CF$_2$OCF=CF$_2$, Br(CF$_2$)$_2$OCF(CF$_3$)CF$_2$OCF=CF$_2$, and I(CF$_2$)$_2$OCF(CF$_3$)CF$_2$OCF=CF$_2$.

In the first step of the reaction disclosed herein, the vinyl ether monomer according to Formula (II) is reacted with a controlled amount of ammonia (NH$_3$) to form the corresponding nitrile molecule, Z—Rf—O—CHF—CN (III), wherein Rf and Z are described above.

Exemplary nitrile molecules according to Formula (III) include: Br(CF$_2$)$_4$OCFHCN, I(CF$_2$)$_4$OCFHCN, CH$_2$=CH(CF$_2$)$_4$OCFHCN, CH$_2$=CHCH$_2$(CF$_2$)$_4$OCFHCN, CH$_2$=CH(CF$_2$)$_2$OCF(CF$_3$)CF$_2$OCFHCN, CH$_2$=CHCH$_2$(CF$_2$)$_2$OCF(CF$_3$)CF$_2$OCFHCN, Br(CF$_2$)$_2$OCF(CF$_3$)CF$_2$OCFHCN, and I(CF$_2$)$_2$OCF(CF$_3$)CF$_2$OCFHCN.

As shown about 3 moles of ammonia are required to form the nitrile molecule. Generally, more moles of ammonia will lead to a faster reaction. In one embodiment, the ratio of ammonia to the vinyl ether monomer of Formula (II) to form the amidine molecule according to Formula (IV) is at least 3 moles of ammonia to 1 mole of the vinyl ether monomer and at most 6, 8, or even 10 moles of ammonia to 1 mole of the vinyl ether monomer.

Addition of ammonia to the vinyl ether monomer can be done from −35° C. to 50° C. Preferably from −10° C. to 25° C. and more preferably from −5° C. to 10° C. Pressure in the reaction can range from 0 psi (pounds per square inch) to 100 psi, preferably from 10 psi to 75 psi and more preferably form 15 psi to 50 psi.

In the second step of the reaction, the corresponding nitrile molecule is reacted with an additional mole of ammonia to form the amidine molecule, Z—Rf—O—CFH—C(=NH)NH$_2$ (IV), wherein Rf and Z are described above.

The ratio of ammonia to the vinyl ether monomer to form the amidine molecule according to Formula (IV) can be from at least 4, 5, 6, or even 7 moles of ammonia to 1 mole vinyl ether monomer.

Exemplary amidine molecules according to Formula (IV) include: Br(CF$_2$)$_4$OCFHC(=NH)NH$_2$, I(CF$_2$)$_4$OCFH(=NH)NH$_2$, CH$_2$=CH(CF$_2$)$_4$OCFH(=NH)NH$_2$, CH$_2$=CHCH$_2$(CF$_2$)$_4$CFH(=NH)NH$_2$, CH$_2$=CH(CF$_2$)$_2$OCF(CF$_3$)CF$_2$OCFH(=NH)NH$_2$, CH$_2$=CHCH$_2$(CF$_2$)$_2$OCF(CF$_3$)CF$_2$OCFH(=NH)NH$_2$, Br(CF$_2$)$_2$OCF(CF$_3$)CF$_2$OCFH(=NH)NH$_2$, and I(CF$_2$)$_2$OCF(CF$_3$)CF$_2$OCFH(=NH)NH$_2$.

The amidine molecule is then heated to a temperature of at least 100° C., 120° C., or even 140° C. and, in some embodiments, at most 200° C., for cyclization of the amidine molecules to form the compound according to Formula (I) along with ammonia.

In the above reaction schemes, typically, a solvent is used to aid the reaction. Preferably, the solvent is a polar aprotic solvent, which has some solubility to the reactants to enable a fast reaction. Preferably, the used solvent is anhydrous in order to eliminate the hydrolysis reaction of nitrile. Solvents that can be used are 1,4 dioxane, methyl-t-butyl ether, glyme, diglyme, tetrahydrofuran, and acetonitrile. Methyl-t-butyl ether is the preferred solvent.

Depending on the reaction product desired, the desired reaction product can be isolated using techniques known in the art. For example, isolation of the nitrile molecule can be done by first filtration of the ammonium fluoride salt, removing the solvent by distillation or rotary evaporation and final distillation to isolate the nitrile molecule. A similar procedure is followed when isolating the amidine molecule, except the amidine molecule is not distilled. In one embodiment, the resulting triazine-containing compound according to Formula (I) is in a purified form, which means the compound according to Formula (I) is at least 75, 80, 85, 90, 95, 98, or even 99 wt (weight) % pure.

The triazine-containing compound as disclosed above, depending on the functional group, Z, may be used as monomer, and/or chain transfer agent in polymerizations of fluoropolymers; and/or may be used as a crosslinking agent in the curing of fluoropolymers.

Polymerization

In one embodiment of the present disclosure, the compound according to Formula (I) is used during the polymerization of fluoropolymers. The compound according to Formula (I), depending on its functionalization (or Z), may be used as a monomer, and/or chain transfer agent during the polymerization of fluoropolymers. For example, when Z is an iodine, the compound according to Formula (I) could be a chain transfer agent, acting to incorporate iodine into the resulting fluoropolymer. For example, when Z is a —CH=CH$_2$, the compound according to Formula (I) could be used as a comonomer, acting to incorporate the triazine ring into the resulting fluoropolymer.

In one embodiment, the compound according to Formula (I) is used along with a fluorinated monomer to generate a fluoropolymer. Such resulting fluoropolymers may be used to generate fluoroplastics and/or fluoroelastomers.

In one embodiment, at least 0.01, 0.05, 0.1, 0.5, 1, 2, 4, or even 5 wt % of the compound according to Formula (I) is used versus the total weight of the fluoropolymer. In one embodiment, at most 0.5, 1, 1.5, 2, 4, 6, 8, 10, 15, or even 20 wt % of the compound according to Formula (I) is used versus the total weight of the fluoropolymer.

The fluorinated monomers used in the polymerization are those known in the art and include TFE (tetrafluoroethylene), VF (vinyl fluoride), VDF (vinylidene fluoride), HFP (hexafluoropropylene), pentafluoropropylene, trifluoroethylene, CTFE (chlorotrifluoroethylene), perfluoro ethers, and combinations thereof.

Exemplary perfluoro ether monomers are of the Formula (VI)

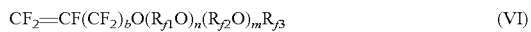

where $R_{f1}$ and $R_{f2}$ are independently linear or branched perfluoroalkylene radical groups comprising 2, 3, 4, 5, or 6 carbon atoms, m and n are independently an integer selected from 0, 1, 2, 3, 4, 5, 6, 7, 8, 9, and 10, and $R_{f3}$ is a perfluoroalkyl group comprising 1, 2, 3, 4, 5, or 6 carbon atoms. Exemplary perfluoroalkyl vinyl ether monomers include: perfluoro (methyl vinyl) ether (PMVE), perfluoro (ethyl vinyl) ether (PEVE), perfluoro (n-propyl vinyl) ether (PPVE-1), perfluoro-2-propoxypropylvinyl ether (PPVE-2), perfluoro-3-methoxy-n-propylvinyl ether, perfluoro-2-methoxy-ethylvinyl ether, perfluoro-methoxy-methylvinylether (CF$_3$—O—CF$_2$—O—CF=CF$_2$), and CF$_3$—(CF$_2$)$_2$—O—CF(CF$_3$)—CF$_2$—O—CF(CF$_3$)—CF$_2$—O—CF=CF$_2$. Exemplary perfluoroalkyl allyl ether monomers include: perfluoro (methyl allyl) ether (CF$_2$=CF—CF$_2$—O—CF$_3$), perfluoro (ethyl allyl) ether, perfluoro (n-propyl allyl) ether, perfluoro-2-propoxypropyl allyl ether, perfluoro-3-methoxy-n-propylallyl ether, perfluoro-2-methoxy-ethyl allyl ether, perfluoro-methoxy-methyl allyl ether, and CF$_3$—(CF$_2$)$_2$—O—CF(CF$_3$)—CF$_2$—O—CF(CF$_3$)—CF$_2$—O—CF$_2$CF=CF$_2$.

In one embodiment, a bisolefin monomer is used during the polymerization. Such bisolefins may be non-fluorinated or fluorinated.

In one embodiment, the bisolefin monomer can be represented by the following formula: CY$_2$=CX-A-CX=CY$_2$ wherein Y is independently selected from H, F, Cl, CH$_3$ or CF$_3$; X is independently selected from H, Cl, F, alkyl or perfluoroalkyl comprising 1 to 3 carbon atoms; and A is an alkylene or cycloalkylene radical, which is non-fluorinated, partially fluorinated, or perfluorinated, comprising 1 to 18 carbon atoms, which can be linear or branched, optionally containing ether linkages.

A is preferably a perfluoroalkylene C$_4$-C$_{12}$ radical, while X and Y are preferably hydrogen, In one embodiment, A is a fluoropolyoxyalkylene radical of the formula

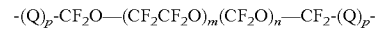

wherein Q is independently selected from an alkylene or oxyalkylene C$_1$-C$_{10}$ radical which can be non-fluorinated, partially fluorinated or perfluorinated; p is 0 or 1; in and n are integers such that the m/n ratio is in the range of 0.2-5 and the molecular weight of the fluoro-polyoxyalkylene radical is in the range of 500-10,000 preferably, 1,000-4,000 Preferably Q is selected from the group consisting of —CH$_2$OCH$_2$—; and —CHO(CH$_2$CH$_2$O)$_s$CH$_2$—, where s is an integer from 1 to 3.

In one embodiment, the fluorinated bisolefin monomer can be represented by the following formula:

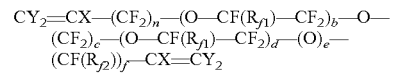

wherein a is an integer selected from 0, 1, and 2; b is an integer selected from 0, 1, and 2; c is an integer selected from 0, 1, 2, 3, 4, 5, 6, 7, and 8; d is an integer selected from 0, 1, and 2; e is 0 or 1; f is an integer selected from 0, 1, 2, 3, 4, 5, and 6; $R_{f1}$ is independently selected from F and CF$_3$; $R_{f2}$ is F or a perfluorinated alkyl group; X is independently selected from H or F; and Y is independently selected from H, F, and CF$_3$. In a preferred embodiment, the bisolefin monomer is perfluorinated, meaning that X and Y are independently selected from F and CF$_3$.

Exemplary fluorinated bisolefin monomers include: CF$_2$=CF—O—(CF$_2$)$_2$—O—CF=CF$_2$, CF$_2$=CF—O—(CF$_2$)$_3$—O—CF=CF$_2$, CF$_2$=CF—O—(CF$_2$)$_4$—O—CF=CF$_2$, CF$_2$=CF—O—(CF$_2$)$_5$—O—CF=CF$_2$, CF$_2$=CF—O—(CF$_2$)$_6$—O—CF=CF$_2$, CF$_2$=CF—CF$_2$—O—(CF$_2$)$_2$—O—CF=CF$_2$, CF$_2$=CF—CF$_2$—O—(CF$_2$)$_3$—O—CF=CF$_2$, CF$_2$=CF—CF$_2$—O—(CF$_2$)$_4$—

O—CF=CF$_2$, CF$_2$=CF—CF$_2$—O—(CF$_2$)$_4$—O—CF=CF$_2$, CF$_2$=CF—CF$_2$—O—(CF$_2$)$_5$—O—CF=CF$_2$, CF$_2$=CF—CF$_2$—O—(CF$_2$)$_6$—O—CF=CF$_2$, CF$_2$=CF—CF$_2$—O—(CF$_2$)$_2$—O—CF$_2$—CF=CF$_2$, CF$_2$=CF—CF$_2$—O—(CF$_2$)$_3$—O—CF$_2$—CF=CF$_2$, CF$_2$=CF—CF$_2$—O—(CF$_2$)$_4$—O—CF$_2$—CF=CF$_2$, CF$_2$=CF—CF$_2$—O—(CF$_2$)$_5$—O—CF$_2$—CF=CF$_2$, CF$_2$=CF—CF$_2$—O—(CF$_2$)$_6$—O—CF$_2$—CF=CF$_2$, CF$_2$=CF—O—CF$_2$CF$_2$—CH=CH$_2$, CF$_2$=CF—(OCF(CF$_3$)CF$_2$)—O—CF$_2$CF$_2$—CH=CH$_2$, CF$_2$=CF—(OCF(CF$_3$)CF$_2$)$_2$—O—CF$_2$CF$_2$—CH=CH$_2$, CF$_2$=CF CF$_2$—O—CF$_2$CF$_2$—CH=CH$_2$, CF$_2$=CF CF$_2$—(OCF(CF$_3$)CF$_2$)—O—CF$_2$CF$_2$—CH=CH$_2$, CF$_2$=CFCF$_2$—(OCF(CF$_3$)CF$_2$)$_2$—O—CF$_2$CF$_2$—CH=CH$_2$, CF$_2$=CF—CF$_2$—CH=CH$_2$, CF$_2$=CF—O—(CF$_2$)$_c$—O—CF$_2$—CF$_2$—CH=CH$_2$ wherein c is an integer selected from 2 to 6, CF$_2$=CFCF$_2$—O—(CF$_2$)$_c$, —O—CF$_2$—CF$_2$—CH=CH$_2$ wherein c is an integer selected from 2 to 6, CF$_2$=CF—(OCF(CF$_3$)CF$_2$)$_b$—O—CF(CF$_3$)—CH=CH$_2$ wherein b is 0, 1, or 2, CF$_2$=CF—CF$_2$—(OCF(CF$_3$)CF$_2$)$_b$—O—CF(CF$_3$)—CH=CH$_2$ wherein b is 0, 1, or 2, CH$_2$=CH—(CF$_2$)$_n$—O—CH=CH$_2$ wherein n is an integer from 1-10, and CF$_2$=CF—(CF$_2$)$_a$—(O—CF(CF$_3$)CF$_2$)$_b$—O—(CF$_2$)$_c$—(OCF(CF$_3$)CF$_2$)$_f$—O—CF=CF$_2$ wherein a is 0 or 1, b is 0, 1, or 2, c is 1, 2, 3, 4, 5, or 6, and f is 0, 1, or 2.

In one embodiment, 0.01 mol % to 1 mol % of the bisolefin monomer is used based on total moles of monomer incorporated into the polymer. In some embodiments, at least 0.02, 0.05, or even 0.1 mol % of the bisolefin monomer is used and at most 0.5, 0.75, or even 0.9 mol % of the bisolefin monomer is used based on the total moles of monomer incorporated into the fluoropolymer.

As known in the art, other copolymerizable monomers, which may or may not contain fluorine substitution, e.g. ethylene, propylene, butylene and the like, may be used during the polymerization. Generally, these additional monomers would be used at less than 25 mole % of the fluoropolymer, preferably less than 10 mole % t, and even less than 3 mole %. The fluoropolymer polymerization can be conducted using known polymerization techniques, however, the fluoropolymers are preferably made through an aqueous emulsion polymerization process, which can be conducted in a known manner including batch, semi-batch, or continuous polymerization techniques. The reactor vessel for use in the aqueous emulsion polymerization process is typically a pressurizable vessel capable of withstanding the internal pressures during the polymerization reaction. Typically, the reaction vessel will include a mechanical agitator, which will produce thorough mixing of the reactor contents and heat exchange system. Any quantity of the monomer(s) may be charged to the reactor vessel. The monomers may be charged batchwise or in a continuous or semi-continuous manner. By semi-continuous it is meant that a plurality of batches of the monomer are charged to the vessel during the course of the polymerization. The independent rate at which the monomers are added to the kettle will depend on the consumption rate of the particular monomer with time. Preferably, the rate of addition of monomer will equal the rate of consumption of monomer, i.e. conversion of monomer into polymer.

The reaction kettle is charged with water, the amounts of which are not critical. To the aqueous phase there is generally also added a fluorinated surfactant, typically a non-telogenic fluorinated surfactant, although aqueous emulsion polymerization without the addition of fluorinated surfactant may also be practiced. When used, the fluorinated surfactant is typically used in amount of 0.010% by weight to 1% by weight. Suitable fluorinated surfactants include any fluorinated surfactant commonly employed in aqueous emulsion polymerization. In one embodiment, the fluorinated surfactants are of the general formula:

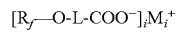

wherein L represents a linear partially or fully fluorinated alkylene group or an aliphatic hydrocarbon group, $R_f$ represents a linear partially or fully fluorinated aliphatic group or a linear partially or fully fluorinated group interrupted with one or more oxygen atoms, $M_i^+$ represents a cation having the valence i and i is 1, 2 and 3. Specific examples are described in, for example, U.S. Pat. No. 7,671,112 (Hintzer et al.). Exemplary emulsifiers include: $CF_3CF_2OCF_2CF_2OCF_2COOH$, $CHF_2(CF_2)_5COOH$, $CF_3(CF_2)_6COOH$, $CF_3O(CF_2)_3OCF(CF_3)COOH$, $CF_3CF_2CH_2OCF_2CH_2OCF_2COOH$, $CF_3O(CF_2)_3OCHFCF_2COOH$, $CF_3O(CF_2)_3OCF_2COOH$, $CF_3(CF_2)_3(CH_2CF_2)_2CF_2CF_2CF_2COOH$, $CF_3(CF_2)_2CH_2(CF_2)_2COOH$, $CF_3(CF_2)_2COOH$, $CF_3(CF_2)_2(OCF(CF_3)CF_2)OCF(CF_3)COOH$, $CF_3(CF_2)_2(OCF_2CF_2)_4OCF(CF_3)COOH$, $CF_3CF_2O(CF_2CF_2O)_3CF_2COOH$, and their salts. In one embodiment, the molecular weight of the surfactant is less than 1500, 1000, or even 500 grams/mole.

These fluorinated surfactants may be used alone or in combination as a mixture of two or more of them. The amount of the surfactant is well below the critical micelle concentration, generally within a range of from 250 to 5,000 ppm (parts per million), preferably 250 to 2000 ppm, more preferably 300 to 1000 ppm, based on the mass of water to be used.

The polymerization is usually initiated after an initial charge of monomer by adding an initiator or initiator system to the aqueous phase. For example, peroxides can be used as free radical initiators. Specific examples of peroxide initiators include, hydrogen peroxide, diacylperoxides such as diacetylperoxide, dipropionylperoxide, dibutyrylperoxide, dibenzoylperoxide, benzoylacetylperoxide, diglutaric acid peroxide and dilaurylperoxide, and further water soluble per-acids and water-soluble salts thereof such as e.g. ammonium, sodium or potassium salts. Examples of per-acids include peracetic acid. Esters of the peracid can be used as well and examples thereof include tert-butylperoxyacetate and tert-butylperoxypivalate. A further class of initiators that can be used are water soluble azo-compounds. Suitable redox systems for use as initiators include for example a combination of peroxodisulphate and hydrogen sulphite or disulphite, a combination of thiosulphate and peroxodisulphate or a combination of peroxodisulphate and hydrazine. Further initiators that can be used are ammonium-alkali- or earth alkali salts of persulfates, permanganic or manganic acid or manganic acids. The amount of initiator employed is typically between 0.03 and 2% by weight, preferably between 0.05 and 10% by weight based on the total weight of the polymerization mixture. The full amount of initiator may be added at the start of the polymerization or the initiator can be added to the polymerization in a continuous way during the polymerization. One can also add part of the initiator at the start and the remainder in one or separate additional portions during the polymerization. Accelerators such as for example water-soluble salts of iron, copper and silver may preferably also be added.

During the initiation of the polymerization reaction, the sealed reactor kettle and its contents are conveniently preheated to the reaction temperature. Polymerization temperatures are from 20° C. to 150° C., preferred from 30° C. to 110° C. and most preferred from 40° C. to 100° C. The polymerization pressure is typically between 4 and 30 bar, in particular 8 to 20 bar. The aqueous emulsion polymerization system may further comprise auxiliaries, such as buffers and complex-formers.

In one embodiment, the fluoropolymer is a copolymer derived from at least the following monomers: hexafluoropropylene (HFP), and vinylidene fluoride (VDF). In one embodiment, the copolymer comprises 25-65% wt % VDF and 15-60 wt % HFP; or even 35-60 wt % VDF and 25-50 wt % HFP.

Additional monomers may also be incorporated into the copolymer, such as TFE, perfluorovinyl ether, and perfluoroallyl ether monomers described above. These additional monomers are typically used at percentages less than 30, 20, 10, 5, or even 1% by weight of the fluoropolymer.

The amount of polymer solids that can be obtained at the end of the polymerization is typically between 10% and 45% by weight, preferably between 20% and 40% by weight.

In one embodiment, the fluoropolymer derived from the compound according to Formula (I) comprises at least 0.01, 0.05, or even 0.1 wt % of I and/or Br; and at most 0.5, 1, 1.5, or even 2 wt % of I and/or Br.

The fluoropolymers derived from the compound according to Formula (I), may then processed, cured, coated, and/or molded as known in the art to form a fluoropolymer article.

Curable Composition

In one embodiment of the present disclosure, the compound according to Formula (I) is combined with a fluorinated elastomeric gum. The fluorinated elastomeric gum comprises a fluoropolymer wherein the fluoropolymer comprises a cure-site (I, Br, and/or CN). The mixture (i.e., the triazine-containing compound and the fluorinated elastomeric gum) is subsequently cured to form a fluoroelastomer.

In one embodiment, the fluoropolymer contains cure sites, which facilitate cross-linking of the fluoropolymer in appropriate cure systems. These cure sites comprise at least one of iodine, bromine, and/or nitrile. The fluoropolymer may be polymerized in the presence of a chain transfer agent and/or cure site monomer to introduce cure sites into the polymer. Such cure site monomers and chain transfer agents are known in the art. Exemplary chain transfer agents include: an iodo-chain transfer agent, a bromo-chain transfer agent, or a chloro-chain transfer agent. For example, suitable iodo-chain transfer agent in the polymerization include the formula of $RI_x$, where (i) R is a perfluoroalkyl or chloroperfluoroalkyl group having 3 to 12 carbon atoms; and (ii) x=1 or 2. The iodo-chain transfer agent may be a perfluorinated iodo-compound. Exemplary iodo-perfluoro-compounds include 1,3-diiodoperfluoropropane, 1,4-diiodoperfluorobutane, 1,6-diiodoperfluorohexane, 1,8-diiodoperfluorooctane, 1,10-diiodoperfluorodecane, 1,12-diiodoperfluorododecane, 2-iodo-1,2-dichloro-1,1,2-trifluoroethane, 4-iodo-1,2,4-trichloroperfluorobutan, and mixtures thereof. In some embodiments, the iodo-chain transfer agent is of the formula $I(CF_2)_n$—O—$R_f$—$(CF_2)_m$I, wherein n is 1, 2, 3, 4, 5, 6, 7, 8, 9, or 10, m is 1, 2, 3, 4, 5, 6, 7, 8, 9, or 10 and $R_f$ is a partially fluorinated or perfluorinated alkylene segment, which can be linear or branched and optionally comprises at least one catenated ether linkage. Exemplary compounds include: I—$CF_2$—$CF_2$—O—$CF_2$—$CF_2$—I, I—$CF(CF_3)$—$CF_2$—O—$CF_2$—$CF_2$—I, I—$CF_2$—$CF_2$—O—$CF(CF_3)$—$CF_2$—O—$CF_2$—$CF_2$—I, I—$(CF(CF_3)$—$CF_2$—O$)_2$—$CF_2$—$CF_2$—I, I—$CF_2$—$CF_2$—O—$(CF_2)_2$—O—$CF_2$—$CF_2$—I, I—$CF_2$—$CF_2$—O—$(CF_2)_3$—O—$CF_2$—$CF_2$—I, and I—$CF_2$—$CF_2$—O—$(CF_2)_4$—O—$CF_2$—$CF_2$—I, I—$CF_2$—$CF_2$—O—$CF_2$—$CF_2$—I, and I—$CF_2$—$CF_2$—$CF_2$—O—$CF(CF_3)$—$CF_2$—O—$CF_2$—$CF_2$—I. In some embodiments, the bromine is derived from a brominated chain transfer agent of the formula: $RBr_x$, where (i) R is a perfluoroalkyl or chloroperfluoroalkyl group having 3 to 12 carbon atoms; and (ii) x=1 or 2. The chain transfer agent may be a perfluorinated bromo-compound.

Cure site monomers, if used, comprise at least one of a bromine, iodine, and/or nitrile cure moiety.

In one embodiment, the cure site monomers may be of the formula: (a) $CX_2$=$CX(Q')$, wherein: (i) X each is independently H or F; and (ii) Q' is I, Br, $R_{f4}$—I or $R_{f4}$—Br and $R_{f4}$=a perfluorinated or partially fluorinated alkylene group optionally containing ether linkages or (b) $Y(CF_2)_qY$, wherein: (i) Y is independently selected from Br or I or Cl and (ii) q=1-6. In addition, non-fluorinated bromo- or iodo-olefins, e.g., vinyl iodide and allyl iodide, can be used. Exemplary cure site monomers include: $CH_2$=CHI, $CF_2$=CHI, $CF_2$=CFI, $CH_2$=$CHCH_2$I, $CF_2$=$CFCF_2$I, $ICF_2CF_2CF_2CF_2$I, $CH_2$=$CHCF_2CF_2$I, $CF_2$=$CFCH_2CH_2$I, $CF_2$=$CFCF_2CF_2$I, $CH_2$=CH$(CF_2)_6CH_2CH_2$I, $CF_2$=$CFOCF_2CF_2$I, $CF_2$=$CFOCF_2CF_2CF_2$I, $CF_2$=$CFOCF_2CF_2CH_2$I, $CF_2$=$CFCF_2OCH_2CH_2$I, $CF_2$=$CFO(CF_2)_3$—$OCF_2CF_2$I, $CH_2$=CHBr, $CF_2$=CHBr, $CF_2$=CFBr, $CH_2$=$CHCH_2$Br, $CF_2$=$CFCF_2$Br, $CH_2$=$CHCF_2CF_2$Br, $CF_2$=$CFOCF_2CF_2$Br, $CF_2$=CFCl, I—$CF_2$—$CF_2CF_2$—O—CF=$CF_2$, I—$CF_2$—$CF_2CF_2$—O—$CF_2CF$=$CF_2$, I—$CF_2$—$CF_2$—O—$CF_2$—CF=$CF_2$, I—$CF(CF_3)$—$CF_2$—O—CF=$CF_2$, I—$CF(CF_3)$—$CF_2$—O—$CF_2$—CF=$CF_2$, I—$CF_2$—$CF_2$—O—$CF(CF_3)$—$CF_2$—O—CF=$CF_2$, I—$CF_2$—$CF_2$—O—$CF(CF_3)$—$CF_2$—O—$CF_2$—CF=$CF_2$, I—$CF_2$—$CF_2$—(O—(CF$(CF_3)$—$CF_2)_2$—O—CF=$CF_2$, I—$CF_2$—$CF_2$—(O—(CF$(CF_3)$—$CF_2)_2$—O—$CF_2$—CF=$CF_2$, Br—$CF_2$—$CF_2$—O—$CF_2$—CF=$CF_2$, Br—$CF(CF_3)$—$CF_2$—O—CF=$CF_2$, I—$CF_2$—$CF_2$—$CF_2$—O—$CF(CF_3)$—$CF_2$—O—CF=$CF_2$, I—$CF_2$—$CF_2$—$CF_2$—O—$CF(CF_3)$—$CF_2$—O—$CF_2$—CF=$CF_2$, I—$CF_2$—$CF_2$—$CF_2$—(O—$(CF(CF_3)$—$CF_2)_2$—O—CF=$CF_2$, I—$CF_2$—$CF_2$—$CF_2$—O—$(CF(CF_3)$—$CF_2$—O)$_2$—$CF_2$—CF=$CF_2$, Br—$CF_2$—$CF_2$—$CF_2$—O—CF=$CF_2$, Br—$CF_2$—$CF_2$—$CF_2$—O—$CF_2$—CF=$CF_2$, I—$CF_2$—$CF_2$—O—$(CF_2)_2$—O—CF=$CF_2$, I—$CF_2$—$CF_2$—O—$(CF_2)_3$—O—CF=$CF_2$, I—$CF_2$—$CF_2$—O—$(CF_2)_4$—O—CF=$CF_2$, I—$CF_2$—$CF_2$—O—$(CF_2)_2$—O—$CF_2$—CF=$CF_2$, I—$CF_2$—$CF_2$—O—$(CF_2)_3$—O—$CF_2$—CF=$CF_2$, I—$CF_2$—$CF_2$—O—$(CF_2)_2$—O—$CF(CF_3)$—$CF_2$—O—$CF_2$—CF=$CF_2$, I—$CF_2$—$CF_2$—O—$(CF_2)_2$—O—CF$(CF_3)CF_2$—O—$CF_2$—CF=$CF_2$, Br—$CF_2$—$CF_2$—O—$(CF_2)_2$—O—CF=$CF_2$, Br—$CF_2$—$CF_2$—O—$(CF_2)_3$—O—CF=$CF_2$, Br—$CF_2$—$CF_2$—O—$(CF_2)_4$—O—CF=$CF_2$, and Br—$CF_2$—$CF_2$—O—$(CF_2)_2$—O—$CF_2$—CF=$CF_2$.

Examples of nitrile containing cure site monomers correspond to the following formula: $CF_2$=CF—$CF_2$—O—Rf—CN; $CF_2$=$CFO(CF_2)_r$CN; $CF_2$=$CFO[CF_2CF(CF_3)$O$]_p$ $(CF_2)_v$$OCF(CF_3)$CN; and $CF_2$=$CF[OCF_2CF(CF_3)]_k$O $(CF_2)_u$CN; wherein, r represents an integer of 2 to 12; p represents an integer of 0 to 4; k represents 1 or 2; v represents an integer of 0 to 6; u represents an integer of 1 to 6; and Rf is a perfluoroalkylene or a bivalent perfluoroether group. Specific examples of nitrile containing fluorinated monomers include, but are not limited to, perfluoro (8-cyano-5-methyl-3,6-dioxa-1-octene), $CF_2$=$CFO(CF_2)_5$ CN, and $CF_2$=$CFO(CF_2)_3OCF(CF_3)$CN.

In one embodiment, the fluoropolymer of the present disclosure comprises at least 0.1, 0.5, 1, 2, or even 2.5 wt % of iodine, bromine, and/or nitrile groups versus the total weight of fluoropolymer. In one embodiment, the fluoropolymer comprises no more than 3, 5, or even 10 wt % of iodine, bromine, and/or nitrile groups versus the total weight of the fluoropolymer.

As used herein, the phrase "fluorinated elastomeric gum" refers to a fluoropolymer that can be processed as a traditional elastomer. To be processed as a traditional elastomer means that the fluoropolymer can be processed with a two-roll mill or an internal mixer. Mill blending is a process that rubber manufacturers use to combine the polymer gum with the requisite curing agents and/or additives. In order to be mill blended, the fluorinated elastomeric gum must have a sufficient modulus. In other words, not too soft that it sticks to the mill, and not too stiff that it cannot be banded onto mill. In one embodiment, the fluorinated elastomeric gum of the present disclosure has a modulus of at least 0.1, 0.3, or even 0.5 MPa (megaPascals); and at most 2.5, 2.2, or even 2.0 MPa at 100° C. as measured at a strain of 1% and a frequency of 1 Hz (Hertz).

The fluorinated elastomeric gum may be perfluorinated or partially fluorinated. As disclosed herein, in a perfluoropolymer, the carbon-hydrogen bonds along the backbone of the fluoropolymer are all replaced with carbon-fluorine bonds and optionally some carbon-chlorine and/or carbon-bromine bonds. It is noted that the backbone of the polymer excludes the sites of initiation and termination of the polymer. As disclosed herein, in a partially fluoropolymer, the polymer comprises at least one carbon-hydrogen bond and at least one carbon-fluorine bond on the backbone of the polymer excluding the sites of initiation and termination of the polymer. In one embodiment, the fluoropolymer is highly fluorinated, wherein at least 50, 60, 70, 80, or even 85% of the polymer backbone comprises C—F bonds and at most 90, 95, or even 99%.

In one embodiment, the fluoropolymer may be derived from one or more fluorinated monomer(s) such as TFE (tetrafluoroethylene), VF (vinyl fluoride), VDF (vinylidene fluoride), HFP (hexafluoropropylene), pentafluoropropylene, trifluoroethylene, CTFE (chlorotrifluoroethylene), perfluoro ethers (as discussed above), and combinations thereof.

It is known by those of skill in the art to modify the fluorinated elastomeric gum during the polymer formation by the addition of small amounts of other copolymerizable monomers, which may or may not contain fluorine substitution, e.g. ethylene, propylene, butylene and the like. Use of these additional monomers (i.e., comonomers) is within the scope of the present disclosure. Generally, these additional monomers would be used at less than 25 mole % of the fluoropolymer, preferably less than 10 mole % t, and even less than 3 mole %.

In one embodiment, the fluorinated elastomeric gum is a random copolymer, which is amorphous, meaning that there is an absence of long-range order (i.e., in long-range order the arrangement and orientation of the macromolecules beyond their nearest neighbors is understood). An amorphous fluoropolymer has no detectable crystalline character by DSC (differential scanning calorimetry), meaning that if studied under DSC, the fluoropolymer would have no melting point or melt transitions with an enthalpy more than 0.002, 0.01, 0.1, or even 1 Joule/g from the second heat of a heat/cool/heat cycle, when tested using a DSC thermogram with a first heat cycle starting at −85° C. and ramped at 10° C./min to 350° C., cooling to −85° C. at a rate of 10° C./min and a second heat cycle starting from −85° C. and ramped at 10° C./min to 350° C. Exemplary amorphous random copolymers may include: copolymers comprising TFE and perfluorinated vinyl ethers monomeric units (such as copolymers comprising TFE and PMVE, and copolymers comprising TFE and PEVE); copolymers comprising TFE and perfluorinated allyl ethers monomeric units; copolymers comprising TFE and propylene monomeric units; copolymers comprising TFE, propylene, and VDF monomeric units; copolymers comprising VDF and HFP monomeric units; copolymers comprising TFE, VDF, and HFP monomeric units; copolymers comprising TFE and ethyl vinyl ether (EVE) monomeric units; copolymers comprising TFE and butyl vinyl ether (BVE) monomeric units; copolymers comprising TFE, EVE, and BVE monomeric units; copolymers comprising VDF and perfluorinated vinyl ethers monomeric units (such as copolymers comprising VDF and $CF_2$=$CFOC_3F_7$) monomeric units; an ethylene and HFP monomeric units; copolymers comprising CTFE and VDF monomeric units; copolymers comprising TFE and VDF monomeric units; copolymers comprising TFE, VDF and perfluorinated vinyl ethers monomeric units (such as copolymers comprising TFE, VDF, and PMVE) monomeric units; copolymers comprising VDF, TFE, and propylene monomeric units; copolymers comprising TFE, VDF, PMVE, and ethylene monomeric units; copolymers comprising TFE, VDF, and perfluorinated vinyl ethers monomeric units (such as copolymers comprising TFE, VDF, and $CF_2$=$CFO(CF_2)_3OCF_3$) monomeric units; and combinations thereof. In one embodiment, the fluoropolymer is not a copolymer comprising VDF and HFP monomeric units.

In one embodiment, the fluorinated elastomeric gum is a block copolymer in which chemically different blocks or sequences are covalently bonded to each other, wherein the blocks have different chemical compositions and/or different glass transition temperatures. In one embodiment, the block copolymer comprises a first block, A block, which is a semi-crystalline segment. If studied under a differential scanning calorimetry (DSC), this block would have at least one melting point temperature ($T_m$) of greater than 70° C. and a measurable enthalpy, for example, greater than 0 J/g (Joules/gram). The second block, or B block, is an amorphous segment, meaning that there is an absence of long-range order (i.e., in long-range order the arrangement and orientation of the macromolecules beyond their nearest neighbors is understood). The amorphous segment has no detectable crystalline character by DSC. If studied under DSC, the B block would have no melting point or melt transitions with an enthalpy more than 2 milliJoules/g by DSC. In one embodiment, the A block is copolymer derived from at least the following monomers: tetrafluoroethylene (TFE), hexafluoropropylene (HFP), and vinylidene fluoride (VDF). In one embodiment, the A block comprises 30-85 wt (weight) % TFE; 5-40 wt % HFP; and 5-55 wt % VDF; 30-75 wt % TFE; 5-35 wt % HFP; and 5-50 wt % VDF; or even 40-70 wt % TFE; 10-30 wt % HFP; and 10-45 wt % VDF. In one embodiment, the B block is a copolymer derived from at least the following monomers: hexafluoropropylene (HFP), and vinylidene fluoride (VDF). In one embodiment, the B block comprises 25-65 wt % VDF and 15-60 wt % HFP; or even 35-60 wt % VDF and 25-50 wt % HFP. Monomers, in addition, to those mentioned above, may be included in the A and/or B blocks. Generally, the weight average of the A block and B block are independently selected from at least 1000, 5000, 10000, or even 25000 daltons; and at most 400000, 600000, or even 800000 daltons. Such block copolymers are disclosed in U.S. Pat. Publ. Nos. 2018-0194888 (Mitchell et al.); and WO Publications 2018/136332 (Mitchell et al.), 2018/136331 (Mitchell et al.), and 2018/136324 (Mitchell et al.); all of which are incorporated herein by reference.

In one embodiment, the amount of the compound of Formula (I) in the curable composition is at least 0.05, 0.1 or even 1 part by weight; and at most 2, 4, 6, or even 10 parts by weight per 100 parts by weight of the fluoropolymer.

The fluoropolymer of the curable composition can be cured with a peroxide curing agent. In one embodiment, the peroxide is an organic peroxide, preferably, a tertiary butyl peroxide having a tertiary carbon atom attached to peroxy oxygen.

Exemplary peroxides include: benzoyl peroxide, dicumyl peroxide, di-tert-butyl peroxide, 2,5-di-methyl-2,5-di-tert-butylperoxyhexane, 2,4-dichlorobenzoyl peroxide, 1,1-bis(tert-butylperoxy)-3,3,5-trimethylchlorohexane, tert-butyl peroxy isopropylcarbonate (TBIC), tert-butyl peroxy 2-ethylhexyl carbonate (TBEC), tert-amyl peroxy 2-ethylhexyl carbonate, tert-hexylperoxy isopropyl carbonate, carbonoperoxoic acid, O,O'-1,3-propanediyl OO,OO'-bis(1,1-dimethylethyl) ester, tert-butylperoxy benzoate, t-hexyl peroxy-2-ethylhexanoate, t-butyl peroxy-2-ethylhexanoate, di(4-methylbenzoyl) peroxide, laurel peroxide and cyclohexanone peroxide. Other suitable peroxide curatives are listed in U.S. Pat. No. 5,225,504 (Tatsu et al.), incorporated herein by reference.

The amount of peroxide used generally will be at least 0.1, 0.2, 0.4, 0.6, 0.8, 1, 1.2, or even 1.5; at most 2, 2.25, 2.5, 2.75, 3, 3.5, 4, 4.5, 5, or even 5.5 parts by weight per 100 parts by weight of the fluoropolymer.

Coagents are reactive additives used to improve the peroxide curing efficiency by rapidly reacting with radicals and potentially suppressing side reactions and/or generating additional crosslinks. The coagent forms a radical through hydrogen abstraction or addition of a radical from the peroxide, which can then react with the polymer through the Br, I, and/or nitrile sites. The coagents are multifunctional polyunsaturated compounds, which are known in the art and include allyl-containing cyanurates, isocyanurates, and phthalates, homopolymers of dienes, and copolymers of dienes and vinyl aromatics. A wide variety of useful coagents are commercially available including di- and tri-allyl compounds, divinyl benzene, vinyl toluene, vinyl pyridine, 1,2-cis-polybutadiene and their derivatives. Exemplary coagents include a diallyl ether of glycerin, triallylphosphoric acid, diallyl adipate, diallylmelamine and triallyl isocyanurate (TAIC), tri(methyl)allyl isocyanurate (TMAIC), tri(methyl)allyl cyanurate, poly-triallyl isocyanurate (poly-TAIC), xylylene-bis(diallyl isocyanurate) (XBD), N,N'-m-phenylene bismaleimide, diallyl phthalate, tris(diallylamine)-s-triazine, triallyl phosphite, 1,2-polybutadiene, ethyleneglycol diacrylate, diethyleneglycol diacrylate, and mixtures thereof. Exemplary partially fluorinated compounds comprising two terminal unsaturation sites include: $CH_2=CH-R_{f1}-CH=CH_2$ wherein $R_{f1}$ may be a perfluoroalkylene of 1 to 8 carbon atoms and a fluorine-containing TAIC such as those disclosed in U.S. Pat. No. 6,191,233 (Kishine et al.), incorporated herein by reference.

In one embodiment, the curable composition comprises a peroxide and a coagent, wherein the amount of coagent used generally will be at least 0.1, 0.5, or even 1 part by weight per 100 parts by weight of the fluoropolymer; and at most 2, 2.5, 3, or even 5 parts by weight per 100 parts by weight of the fluoropolymer.

Curable Compositions and Processing

The curable compositions can also contain a wide variety of additives of the type normally used in the preparation of elastomeric compositions, such as acid acceptors, process aides, pigments, fillers, pore-forming agents, and those known in the art.

Such fillers include: an organic or inorganic filler such as clay, silica ($SiO_2$), alumina, iron red, talc, diatomaceous earth, barium sulfate, wollastonite ($CaSiO_3$), calcium carbonate ($CaCO_3$), calcium fluoride, titanium oxide, iron oxide and carbon black fillers, a polytetrafluoroethylene powder, PFA (TFE/perfluorovinyl ether copolymer) powder, an electrically conductive filler, a heat-dissipating filler, and the like may be added as an optional component to the composition. Those skilled in the art are capable of selecting specific fillers at required amounts to achieve desired physical characteristics in the cured product. The filler components may result in a cured product that is capable of retaining a preferred elasticity and physical tensile, as indicated by an elongation and tensile strength value, while retaining desired properties such as retraction at lower temperature (TR-10).

In one embodiment, the curable composition and/or cured product comprises less than 40, 30, 20, 15, or even 10% by weight of the filler.

Conventional adjuvants may also be incorporated into the curable composition of the present disclosure to enhance the properties in the resulting cured product. For example, acid acceptors may be employed to facilitate the cure and thermal stability of the compound. Suitable acid acceptors may include magnesium oxide, lead oxide, calcium oxide, calcium hydroxide, dibasic lead phosphite, zinc oxide, barium carbonate, strontium hydroxide, calcium carbonate, hydrotalcite, alkali stearates, magnesium oxalate, or combinations thereof. The acid acceptors are preferably used in amounts ranging from at least 1, 2, 4, or even 5%; and at most 10, 15, or even 20% weight per weight of the fluoropolymer.

In one embodiment, the curable compositions (and the resulting cured articles) are substantially free of inorganic acid acceptors, meaning that the curable composition (or resulting cured article) contains less than 0.5, 0.1, 0.05, 0.01% be weight per weight of the fluoropolymer, or even no inorganic acid acceptor.

The curable fluoropolymer compositions may be prepared by mixing the triazine-containing compound of Formula (I), the fluoropolymer, and any additional components in conventional rubber processing equipment to provide a solid mixture, i.e. a solid polymer containing the additional ingredients, also referred to in the art as a "compound". This process of mixing the ingredients to produce such a solid polymer composition containing other ingredients is typically called "compounding". Such equipment includes rubber mills, internal mixers, such as Banbury mixers, and mixing extruders. The temperature of the mixture during mixing typically will not rise above about 120° C. During mixing, the components and additives are distributed uniformly throughout the resulting fluoropolymer "compound" or polymer sheets. The "compound" can then be extruded or pressed in a mold, e.g., a cavity or a transfer mold and subsequently be oven-cured. In an alternative embodiment, curing can be done in an autoclave.

Pressing of the compounded mixture (i.e., press cure) is typically conducted at a temperature of about 120-220° C., preferably about 140-200° C., for a period of about 1 minute to about 15 hours, usually for about 1-15 minutes. A pressure of about 700-20,000 kPa, preferably about 3400-6800 kPa, is typically used in molding the composition. The molds first may be coated with a release agent and prebaked.

The molded vulcanizate can be post cured in an oven at a temperature of about 140-240° C., preferably at a temperature of about 160-230° C., for a period of about 1-24 hours or more, depending on the cross-sectional thickness of the sample. For thick sections, the temperature during the post cure is usually raised gradually from the lower limit of the range to the desired maximum temperature. The maximum temperature used is preferably about 260° C., and is held at this value for about 1 hour or more.

In one embodiment, the compound according to Formula (I) is more compatible with a fluoropolymer than, for example TAIC, enabling better incorporation into the curable composition and better performance of the resulting fluoroelastomer.

The cured fluoroelastomer is particularly useful as hoses, seals, gaskets, and molded parts in automotive, chemical processing, semiconductor, aerospace, and petroleum industry applications, among others.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Millipore, Saint Louis, Missouri, or may be synthesized by conventional methods.

The following abbreviations are used in this section: g=grams, cm=centimeters, min=minutes, h=hours, pC=degrees Celsius, ° F.=degrees Farenheit, MPa=megapascals, mol=moles, wt %=weight percent, L=liters, mL=milliLiters, NMR=nuclear magnetic resonance, FTIR=Fourier transform infrared spectrophotometry, DSC=differential scanning calorimetry, J=Joules. Abbreviations for materials used in this section, as well as descriptions of the materials, are provided in Table 1.

The abbreviations in Table 1 (below) are used for materials throughout the Examples.

Test Methods $^1$H- and $^{19}$F-Nuclear Magnetic Resonance (NMR) Test Method

NMR spectra were acquired using Agilent VNMRS 400 and Bruker Avance-III HD 600 FT-NMR spectrometers. The Agilent FT-NMR system was operating with a 5-mm inverse-detection gradient probe at an analysis temperature of 22-23° C. The Bruker FT-NMR system was operating with a helium cooled 5-mm inverse-detection gradient TCI cryoprobe at an analysis temperature of 25° C. The sample was dissolved in deuterated acetone (acetone-d$_6$) for analysis and then the solution was spiked with a small amount of CFCl$_3$ for NMR analyses. Initial 1D 400 MHz & 600.1 MHz $^1$H-NMR spectra, 376.3 MHz and 564.7 MHz $^{19}$F-NMR spectra, and qualitative 150.8 MHz $^{13}$C-NMR spectra were acquired. The CFCl$_3$ was added for use as the $^{19}$F-NMR chemical shift zero calibration reference standard. Various 2D NMR experiments were performed to facilitate assignment of the signals observed in the 1D spectra.

Cure Rheology

Cure rheology tests were carried out using uncured, compounded samples using a rheometer (PPA 2000 by Alpha technologies, Akron, Ohio), in accordance with ASTM D 5289-93A at 177° C., no pre-heat, 12 minute elapsed time, and a 0.5 degree arc. Both the minimum torque ($M_L$) and highest torque attained during a specified period of time when no plateau or maximum torque ($M_H$) was obtained were measured. Also reported were the time for the torque to reach a value equal to $M_L+0.5(M_H-M_L)$, (t'50), and the time for the torque to reach $M_L+0.9(M_H-M_L)$, (t'90). Results are reported in Table 3.

TABLE 1

| Abbreviation | Description and Source |
|---|---|
| MA3 | CF$_3$CF$_2$CF$_2$OCF$_2$CF=CF$_2$ prepared as described in U.S. Pat. No. 5,891,965 (Worm et al.) as PPAE-2 |
| MV4E | CH$_2$=CH(CF$_2$)$_4$OCF=CF$_2$ prepared as described in U.S. Pat. Pub. 20160083489 (Grootaert, et al) |
| MV4I | I(CF$_2$)$_4$OCF=CF$_2$ prepared as described in U.S. Pat. Pub. 20160083489 (Grootaert, et al) |
| Ammonia | Anhydrous, Millipore-Sigma, Milwaukee, Wisconsin |
| Methyl tert-butyl ether | Millipore-Sigma |
| APS | Ammonium Persulfate, Millipore-Sigma, Milwaukee, Wisconsin. |
| Potassium Phosphate | K$_2$HPO$_4$, Millipore-Sigma, Milwaukee, Wisconsin. |
| Emulsifier | An aqueous solution comprising 30% by weight of CF$_3$OCF$_2$CF$_2$CF$_2$OCHFCF$_2$CO$_2$NH$_4$ and spiked with a 1.5% wt of a fluorinated liquid commercially available under the trade designation "FLUORINERT FC-70" from 3M Co., St. Paul, MN. CF$_3$OCF$_2$CF$_2$CF$_2$OCHFCF$_2$CO$_2$NH$_4$ is the ammonium salt of the compound prepared as in "Preparation of Compound 11" in U.S. Pat. No. 7,671,112 (Hintzer et al.). |
| Fluoropolymer A | A fluoroelastomer derived from 23 wt % TFE, 41 wt % HFP, and 36 wt % VDF with 70 wt % fluorine content, 0.3 wt % iodine content, and Mooney Viscosity ML1 + 10 at 121° C. of 20 |
| Fluoropolymer B | A perfluoroelastomer derived from about 49.2% of TFE, 50.3% of perfluoromethyl vinyl ether (PMVE) and 0.5% of CF$_2$=CFO(CF$_2$)$_3$O(CF$_2$)$_2$I by weight, 72.2% fluorine content by weight, 0.31% iodine content by weight and Mooney Viscosity ML1 + 10 at 121° C. of 35 |
| N990 | Carbon black obtained under the trade designation "N990" from Cancarb, Medicine Hat, AB, CA |
| TAIC | Triallyl-isocyanurate obtained under the trade designation "TAIC" from Nippon Kasei Chemical Co. Ltd., Tokyo, Japan |
| DBPH-50 | 2,5-dimethyl-2,5-di(t-butylperoxy)-hexane, 50% active, obtained under the trade designation "VAROX DBPH-50" from Vanderbilt Chemicals, LLC., Norwalk, CT |

Physical Properties

Tensile, elongation, and modulus data were gathered from both press and post cured samples cut at room temperature to Die D specifications in accordance with ASTM 412-06A.

Molded O-Rings and Compression Set

O-rings (214, AMS AS568) were molded at 177° C. for 10 minutes at 400 kPa. The press cured O-rings were post cured at 250° C. for 16 hours. The post cured O-rings were tested for compression set for 70 hours at 200° C. in accordance with ASTM D 395-03 Method B and ASTM D1414-94 with a 25% deflection. Results are reported as percentages.

Comparative Example a (Comp. Ex. A): Reaction of Perfluoropropyl Ally Ether, $CF_3CF_2CF_2OCF_2CF=CF_2$ with Ammonia A 600 milliliter (mL) reactor (Parr Instrument Company, Moline, IL, USA) was evacuated to 25 millimeter (mm) vacuum. The vacuum evacuated reactor was then charged with 50 grams (0.16 mol) MA3 along with 150 grams of methyl tert-butyl ether. The reactor was stirred and cooled to −2° C. The addition of 13 grams (0.77 mol) ammonia was then metered into the reactor over thirty minutes. No temperature increase was noted during the ammonia addition. The reactor was then warmed to 25° C. and the mixture was drained. The brown-colored slurry was washed with 250 grams deionized water and the top brown-colored organic phase was distilled to recover solvent with unreacted MA3. The product remaining after distillation of MA3, was analyzed. The product contained $CF_3CF_2CONH_2$ amide by-product and no amidine product was identified by FTIR and NMR.

Example 1 (Ex. 1): Preparation of $(CH_2=CH(CF_2)_4 OCFH)_3$—$C_3N_3$, $(1H-MV4E)_3$-Triazine A 600 mL Parr reactor was evacuated to 25 mm vacuum. The vacuum evacuated reactor was charged with 100 grams (0.3 mol) MV4E along with 250 grams of methyl tert-butyl ether. The reactor was then stirred and cooled to −2° C. The addition of 27 grams (1.6 mol) ammonia was metered into the reactor over two hours which caused the temperature to rise to 2° C. The reactor was then vented to release excess ammonia. After the initial venting, the reactor was warmed to 25° C. and excess ammonia was vented again. The mixture was then stirred at 25° C. for 20 hours. The resulting slurry was filtered through a glass-fritted funnel and the solvent was removed by atmospheric distillation. After the solvent was removed, the oil bath was set to 144° C. and held at that temperature for thirty minutes. Off-gassing was monitored through a bubbler. Heating was then stopped and the flask was cooled to 25° C. FTIR analysis showed a strong peak at 1564 cm$^{-1}$ for the triazine formation. Vacuum pressure was set at 11 mm to remove any volatiles and gave 79.4 grams (0.09 mol) $(CH_2=CHC_4F_8—CFH)_3$—$C_3N_3$, $(1H-MV4E)_3$-Triazine for an 85% yield. $^1$H- and $^{19}$F-NMR confirmed the desired compound. GC/MS gave 96.3% purity.

Example 2 (Ex. 2): Preparation of $[I(CF_2)_4 OCFH]_3$—$C_3N_3$, $(1H-MV4I)_3$-Triazine A 600 mL Parr reactor was evacuated to 25 mm vacuum. The vacuum evacuated reactor was then charged with 100 grams (0.2 mol) MV4I along with 200 g of methyl tert-butyl ether. The reactor was stirred and cooled to −2° C. The addition of 12.5 grams (0.7 mol) ammonia was metered into the reactor over thirty minutes, which caused the temperature to rise to 4° C. The reactor was then warmed to 25° C. and the mixture was drained. The resulting slurry was filtered through a glass-fritted funnel and the solvent was removed by rotary evacuation. Vacuum distillation gave 51 grams (0.13 mol) $IC_4F_8OCFHCN$ (boiling point of 80° C. at 51 mm vacuum) for a 54% yield of iodohydrofluoronitrile and 16.7 grams (0.014 mol) $[I(CF_2)_4OCFH]_3$—$C_3N_3$, $(1H-MV4I)_3$-Triazine (boiling point of 194° C. at 10 mm Hg) for an 18% yield. $^1$H- and $^{19}$F-NMR confirmed $[I(CF_2)_4 OCFH]_3$—$C_3N_3$. GC/MS gave 74% purity.

Example 3: Polymerization

The traizine-containing molecule from Ex. 2 was used in the polymerization of VDF and HFP. A 4 L reactor was charged with 2250 g of deionized water and heated to 74° C. The agitator rate was then brought to 650 rpm (revolutions per minute), followed by additions of 5.1 g of potassium phosphate, 20 g of $(1H-MV4I)_3$-triazine, 33 g of emulsifier, and 5.1 g of APS. Immediately following this addition, the vacuum was broken with HFP to 53 psig (0.37 MPa), followed by addition of VDF to a pressure of 160 psig (1.10 MPa). Once at pressure, monomer weight ratios were changed to HFP/VDF of 0.651. An additional 285 g of deionized water was added during the processing to dissolve solid reagents and for rinsing after delivery of the reagents. The reaction was run until 36% solids, stopped, and the latex was then coagulated using a 1.25% magnesium chloride solution in deionized water, and oven dried at 130° C. for 16 hrs. The resulting polymer was analyzed by NMR to investigate $(1-HMV4I)_3$—$C_3N_3$ used as a chain transfer agent. The results, presented in Table 2, show $(1-HMV4I)_3$—$C_3N_3$ incorporated into the copolymer.

TABLE 2

| Fluoroelastomer Sub-Structures | $^1$H/$^{19}$F-NMR Relative Mole % Concentrations | $^1$H/$^{19}$F-NMR Relative Wt. % Concentrations |
|---|---|---|
| VDF: Vinylidene fluoride (Mol. Wt.* = 64.035) | 74.7% | 55.6% |
| HFP: Hexafluoropropylene (Mol. Wt. = 150.024) | 24.4% | 42.6% |
| R—$CF_2$—H (Mol. Wt. = 51) end/pendent group | 0.37% | 0.22% |
| R—$CF_2$—$CH_3$ (Mol. Wt. = 65) end/pendent groups | 0.09% | 0.07% |
| R—$CF_2CH_2$—I end/pendent groups (Mol. Wt. = 191) | 0.14% | 0.31% |

TABLE 2-continued

| Fluoroelastomer Sub-Structures | $^1H/^{19}F$-NMR Relative Mole % Concentrations | $^1H/^{19}F$-NMR Relative Wt. % Concentrations |
|---|---|---|
| Possible 1H-MV4I triazine initiator [1] (Mol. Wt. = 822.2) | 0.06% | 0.54% |
| R—CF$_2$—CH$_2$OH (Mol. Wt. = 81) end/pendent groups | 0.05% | 0.05% |
| R—CF$_2$—CH$_2$CF$_2$—I & R—CF$_2$—CH$_2$—CH$_2$CF$_2$—I end/pendent groups (Mol. Wt. = 191) | 0.09% | 0.21% |

*Mol. Wt. = molecular weight in g/mol

Example 4

A 4 L reactor was charged with 2250 g of deionized water and heated to 74° C. The agitator rate was then brought to 650 rpm, followed by additions of 5.1 g of potassium phosphate, 20 g of (1H-MV4E)3-Triazine, 33 g of emulsifier, and 5.1 g of APS. Immediately following this addition, the vacuum was broken with HFP to 53 psig (0.37 MPa), followed by addition of VDF to a pressure of 160 psig (1.10 MPa). Once at pressure, monomer weight ratios were changed to HFP/VDF of 0.651. An additional 285 g of deionized water was added during the processing to dissolve solid reagents and for rinsing after delivery of the reagents. The reaction was run until 21% solids, stopped, and the latex was then coagulated using a 1.25% magnesium chloride solution in deionized water, and oven dried at 130° C. for 16 hrs.

Examples 5-8 (Ex. 5-Ex. 8) and Comparative Example 2 (CE 2)

200 gram polymer batches were made by compounded the materials and amounts listed in Table 3 on a two-roll mill. The rheology and physical properties are shown in Table 4 below.

TABLE 3

| Material | Ex. 5 | Ex. 6 | Ex. 7 | Ex. 8 | CE 2 |
|---|---|---|---|---|---|
| Fluoropolymer A | | | 100 | 100 | 100 |
| Fluoropolymer B | 100 | 100 | | | |
| N990 | 30 | 30 | 30 | 30 | 30 |
| 1H MV4E Triazine | 3.63 | | 3.63 | | |
| 1H MV4I Triazine | | | | | 7.2 |
| TAIC | | 1 | | 1 | |
| DPBH-50 | 2 | 2 | 2 | 2 | 2 |

TABLE 4

| | Ex. 5 | Ex. 6 | Ex. 7 | Ex. 8 | CE 2 |
|---|---|---|---|---|---|
| Cure rheology (177° C., 12 minutes) | | | | | |
| M$_L$, Minimum Torque, dNm | 0.6 | 1.1 | 0.6 | 0.8 | 0.3 |
| M$_H$, Maximum Torque, dNm | 18.5 | 33.8 | 8.8 | 20.8 | 0.3 |
| t'50, Time to 50% cure-minutes | 1.3 | 0.4 | 2.2 | 0.6 | 1.99 |
| t'90, Time to 90% cure-minutes | 2.9 | 0.7 | 5.8 | 1.3 | 2.00 |
| Press Cure at 177° C. (350° F.), 10 minutes | | | | | |
| Tensile, MPa | 12.7 | 16.0 | 11.4 | 14.1 | NM |
| Elongation at break, % | 221 | 167 | 465 | 289 | NM |
| 50% Modulus, MPa | 2.7 | 3.7 | 1.3 | 1.5 | NM |
| 100% Modulus, MPa | 5.9 | 10.2 | 1.9 | 3.1 | NM |
| Hardness, Shore A | 70 | 75 | 65 | 67 | NM |
| Post Cure at 250° C. (482° F.), 16 hours | | | | | |
| Tensile, MPa | 17.5 | 20.5 | 14.8 | 20.7 | NM |
| Elongation at break, % | 189 | 160 | 406 | 252 | NM |
| 50% Modulus, MPa | 3.5 | 4.8 | 1.7 | 1.8 | NM |
| 100% Modulus, MPa | 8.6 | 13.0 | 2.7 | 4.1 | NM |
| Hardness, Shore A | 76 | 76 | 67 | 68 | NM |
| Compression Set 70 hours at 200° C., 25% deflection | | | | | |
| Post cure | 44 | 19 | 59 | 34 | NM |
| Compression Set 70 hours @ 232° C., 25% deflection | | | | | |
| Post cure | 64 | 56 | 90 | 73 | NM |

NM = not measured

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will prevail.

What is claimed is:

1. A curable composition comprising (a) a fluorinated elastomeric gum comprising a fluoropolymer, wherein the fluoropolymer comprises a —I cure site, a —Br cure site, a —CN cure site, or combinations thereof; (b) a peroxide; and (c) a compound of Formula (I)

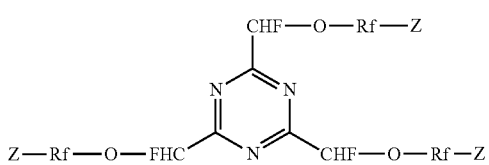

wherein Rf is a perfluorinated divalent group comprising 2 to 12 carbon atoms, and Z is —CH=CH$_2$, or —CH$_2$CH=CH$_2$.

2. The curable composition of claim 1, wherein the molecular weight of the compound of Formula (I) is less than 1500 grams/mole.

3. The curable composition of claim 1, wherein Rf is a —(CF$_2$)$_n$—, where n is an integer from 2 to 8.

4. The curable composition of claim 1, wherein Rf comprises —(CF$_2$)$_p$—O—(CF$_2$)$_q$—, —(OCF$_2$CF$_2$)$_q$—, —(OCF$_2$CF(CF$_3$))$_p$— —(CF$_2$CF(CF$_3$))$_p$—O—(CF$_2$)$_q$—, or combinations thereof, wherein p is an integer of 2 to 11 and q is an integer from 2 to 11, such that the sum of p+q is 2 to 12.

5. The curable composition of claim 1, wherein the compound according to Formula (I) is at least one of the following: [Br—(CF$_2$)$_4$OCFH]$_3$—C$_3$N$_3$, [I—(CF$_2$)$_4$OCFH]$_3$—C$_3$N$_3$, [CH$_2$=CH—(CF$_2$)$_4$OCFH]$_3$—C$_3$N$_3$, [CH$_2$=CHCH$_2$—(CF$_2$)$_4$OCFH]$_3$—C$_3$N$_3$, [CH$_2$=CH—(CF$_2$)$_2$OCF(CF$_3$)CF$_2$OCFH]$_3$—C$_3$N$_3$, [CH$_2$=CHCH$_2$—(CF$_2$)$_2$OCF(CF$_3$)CF$_2$OCFH]$_3$—C$_3$N$_3$, [Br—(CF$_2$)$_2$OCF(CF$_3$)CF$_2$OCFH]$_3$—C$_3$N$_3$, and [I—(CF$_2$)$_2$OCF(CF$_3$)CF$_2$OCFH]$_3$—C$_3$N$_3$, where C$_3$N$_3$ represents the triazine ring.

6. The curable composition of claim 1, comprising at least 0.05 part by weight of the compound of Formula (I) to 100 parts by weight of the fluoropolymer.

7. The curable composition of claim 1, wherein the peroxide comprises 2,5-dimethyl-2,5-di(t-butylperoxy) hexane; dicumyl peroxide; di(2-t-butylperoxyisopropyl) benzene; dialkyl peroxide; bis (dialkyl peroxide); 2,5-dimethyl-2,5-di(tertiarybutylperoxy)$_3$-hexyne; dibenzoyl peroxide; 2,4-dichlorobenzoyl peroxide; tertiarybutyl perbenzoate; α,α'-bis(t-butylperoxy-diisopropylbenzene); t-butyl peroxy isopropylcarbonate, t-butyl peroxy 2-ethylhexyl carbonate, t-amyl peroxy 2-ethylhexyl carbonate, t-hexylperoxy isopropyl carbonate, di[1,3-dimethyl-3-(t-butylperoxy)butyl] carbonate, carbonoperoxoic acid, O,O'-1,3-propanediyl OO,OO'-bis(1,1-dimethylethyl) ester, or combination thereof.

8. The curable composition of claim 1, wherein the fluoropolymer comprises: (i) a copolymer comprising tetrafluoroethylene, vinylidene fluoride, and hexafluoropropylene monomeric units; (ii) a copolymer comprising tetrafluoroethylene, and propylene monomeric units; (iii) a copolymer comprising tetrafluoroethylene, vinylidene fluoride, and propylene monomeric units; and (iv) a copolymer comprising vinylidene fluoride, perfluoro (methyl vinyl) ether, and hexafluoropropylene monomeric units; (v) a copolymer comprising tetrafluoroethylene, vinyl fluoride, and hexafluoropropylene monomeric units; (vi) a copolymer comprising vinyl fluoride, perfluoro (methyl vinyl) ether, and hexafluoropropylene monomeric units; (vii) a copolymer of tetrafluoroethylene with perfluorovinyl ether, (viii) a copolymer of tetrafluoroethylene with perfluoroallyl ether, or combinations thereof.

9. The curable composition of claim 1, comprising at least 0.05 parts by weight of the peroxide per 100 parts of the fluoropolymer.

10. A cured article derived from the curable composition of claim 1.

11. The cured article of claim 10, wherein the article is an o-ring, a seal, a gasket, a hose or a sheet.

12. A compound according to Formula (I):

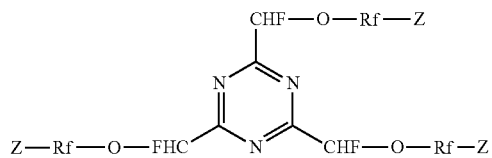

wherein Rf is a perfluorinated divalent group comprising 2 to 12 carbon atoms; and Z is —I, —Br, —CH=CH$_2$, or —CH$_2$CH=CH$_2$.

13. The compound of claim 12, wherein Rf is —(CF$_2$)$_m$—, where m is an integer from 2 to 8.

14. The compound of claim 12, wherein Rf comprises at least one catenated oxygen or nitrogen atom.

15. The compound of claim 12, wherein Formula (I) is: (Br(CF$_2$)$_4$OCFH)$_3$—C$_3$N$_3$, (I(CF$_2$)$_4$OCFH)$_3$—C$_3$N$_3$, (CH$_2$=CH(CF$_2$)$_4$OCFH)$_3$—C$_3$N$_3$, (CH$_2$=CHCH$_2$(CF$_2$)$_4$OCFH)$_3$—C$_3$N$_3$, (CH$_2$=CHC(CF$_2$)$_2$OCF(CF$_3$)CF$_2$OCFH)$_3$—C$_3$N$_3$, (CH$_2$=CHCH$_2$(CF$_2$)$_2$OCF(CF$_3$)CF$_2$OCFH)$_3$—C$_3$N$_3$, (Br(CF$_2$)$_2$OCF(CF$_3$)CF$_2$OCFH)$_3$—C$_3$N$_3$, (I(CF$_2$)$_2$OCF(CF$_3$)CF$_2$OCFH)$_3$—C$_3$N$_3$, or combinations thereof, where C$_3$N$_3$ represents the triazine ring.

16. A fluoropolymer derived from (a) a fluorinated monomer, and (b) a compound of Formula (I)

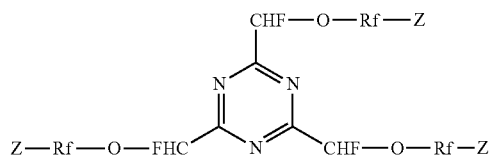

wherein Rf is a perfluorinated divalent group comprising 2 to 12 carbon atom; and Z is —Br, —CH=CH$_2$, or —CH$_2$CH=CH$_2$.

17. The fluoropolymer of claim 16, further derived from a bisolefin monomer.

18. The fluoropolymer of claim 16, wherein Z is —CH=CH$_2$, or —CH$_2$CH=CH$_2$ and the polymer is derived from less than 1.0 moles of the compound according to Formula (I).

* * * * *